United States Patent [19]
Camerini-Otero et al.

[11] Patent Number: 5,510,473
[45] Date of Patent: Apr. 23, 1996

[54] CLONING OF THE RECA GENE FROM THERMUS AQUATICUS YT-1

[75] Inventors: Rafael D. Camerini-Otero, Kensington; Evelina Angov, Bethesda, both of Md.

[73] Assignee: The United States of American as represented by the Secretary of Health and Human Services, Washington, D.C.

[21] Appl. No.: 97,831

[22] Filed: Jul. 26, 1993

Related U.S. Application Data

[63] Continuation-in-part of Ser. No. 41,341, Apr. 1, 1993, abandoned, and Ser. No. 89,910, Jul. 12, 1993, which is a continuation of Ser. No. 733,744, Jul. 24, 1991, abandoned, which is a continuation-in-part of Ser. No. 611,268, Nov. 9, 1990, abandoned, said Ser. No. 41,341, is a continuation of Ser. No. 611,268.

[51] Int. Cl.$^6$ .......................... C12N 15/32; C12N 15/70; C12N 15/00
[52] U.S. Cl. ...................... 530/23.5; 530/23.1; 530/23.7; 435/252.3; 435/252.33; 435/320.1; 935/14
[58] Field of Search ................................. 536/23.7, 23.1, 536/23.5; 435/320.1, 172.3, 252.33, 242.33; 935/14, 73

[56] References Cited

U.S. PATENT DOCUMENTS 5,223,414  6/1993  Zarling et al. ..................... 435/91.2

OTHER PUBLICATIONS

Alberts et al., *Molecular Biology of the Cell*, 1983, Garland Publishing, Inc., New York, NY, pp. 162–163.
USB Molecular Biology Reagents/Protocols 1992, United States Biochemical, p. 618.
Sano et al., Molec. Gen. Genet. 208: 412 (1987).
Berson et al., Nucleic Acids. Res. 18: 675 (1990).
Suggs et al., Proc. Natl. Acad. Sci. USA 78: 6613 (1981).
Marcus–Sekura, Anal. Biochem. 172: 289 (1988).
Frances C. Lawyer, et al.; The Journal of Biological Chemistry vol. 264, No. 11, Apr. 15, pp. 6427–6437; "Isolation, Characterization, and Expression in Escherichia coli of the DNA Polymerase Gene from Thermus aquaticus".
V. V. Mozhaev, et al.; Review, Enzyme Microb. Technol, 1984, vol. 6, pp. 50–59 Feb.; "Structure–Stability relationships in proteins: new approaches to stabilizing enzymes".
Yasuo Kagawa, et al.; The Journal of Biological Chemistry; vol. 259, No. 5, Mar. 10, pp. 2956–2960, 1984; "High Guanine plus Cytosine Content in the Third Letter of Codons of an Extreme Thermophile".
Osamu Nureki, et al.; The Journal of Biological Chemistry, vol. 266, No. 5, Feb. 15, pp. 3268–3277, 1991; "Methionyl–tRNA Synthetase Gene From and Extreme Thermophile, Thermus thermophilus HB8".
Peggy Hsieh, et al.; Proc. Natl. Acad. Sci. USA; vol. 89, pp. 6492–6496, Jul. 1992; Biochemistry; "The synapsis event in the homologous pairing of DNAs: RecA recognizes and pairs less than one helical repeat of DNA".
Alberto I. Roca, et al.; Biochemistry and Molecular Biology; vol. 25, Issue 6; pp. 415–456; "The RecA Protein: Structure and Function" (1990).
Marcia Barinaga, Research News; 27 Sep. 1991; "Will 'DNA Chip' Speed Genome Initiative?".
Denise Casey, Human Genome News, Jan. 1993; pp. 3–4; "DNA Chip Promises Faster Sequencing".
Peggy Hsieh, et al.; The Journal of Biological Chemistry; vol. 264, No. 9, Mar. 25; pp. 5089–5097; "Formation of Joint DNA Molecules by Two Eukaryotic Strand Exhange Proteins Does Not Require Melting of a DNA Duplex".
Peggy Hsieh, et al.; Genes & Development; 4:1951–1963; 1990; "Pairing of homologous DNA sequences by proteins: evidence for three–stranded DNA".
Akira Shinohara, et al.; Cell, vol. 69, 457–470; May 1, 1992; "Rad51 Protein Involved in Repair and Recombination in S. cerevisiae is a RecA–like Protein".
Derrick Bowen, et al.; Biochem. J., (1988), 254, 509–517; "Nucleotide sequence of the phosphoglycerate kinase gene from the etreme thermophile Thermus thermophilus".
L. V. Venkatesh, et al.; Gene 113; 1992 Elsevier Science Publishers; pp. 47–53; "The Azotobacter vinelandii recA gene: sequence analysis and regulation of expression".
T. Nakazawa, et al.; Gene 94, Elsevier (1990) pp. 83–88; "Cloning, sequencing and transcriptional analysis of the recA gene of Pseudomonas cepacia".
Douglas K. Bishop, et al.; Cell, vol. 69, May 1, 1992; pp. 439–456; "DMC1: A Meiosis–Specific Yeast Homolog of E. coli recA Required for Recombination, Synaptonemal Complex Formation, and Cell Cycle Progression".
Michael M. Cox. Ann. Rev. Biochem. 1987; 56: 229–62; "Enzymes of General Recombination".
James G. Wetmur et al.; FASEB Summer Conference; Jul. 25–30; 1993; "Cloning, Sequencing and Expression of Three Distantly Related Thermophilic RecA Proteins".

*Primary Examiner*—James Martinell
*Attorney, Agent, or Firm*—Knobbe Martens Olson & Bear

[57] ABSTRACT

The present invention includes the isolation of an oligonucleotide encoding *Thermus aquaticus* recA protein, and to the purified protein. The invention also includes methods of use of the protein, particularly, methods for hybridizing a primer to a complementary template with increased binding affinity at a temperature above 45° C.

6 Claims, 3 Drawing Sheets

T. aquaticus (SEQ ID NO:2)

E. coli (SEQ ID NO:6)

```
1     MEENKRKSLENALKTIEKEFGKGAVMRLGEMPKLQVDVIPTGSLGLDL  48
      ::|||.|.|..||   |||:||||.:|||||  ..::|:.|.||||:||:
1     MAIDENKQKALAAALGQIEKQFGKGSIMRLGEDRSMDVETISTGSLSLDI  50

49    ALGIGGIPRGRVTEIFGPESGGKTTLALTIIAQAQKGGGVAAFVDAEHAL  98
      |||  ||:|.||:.||||||:||||||.|  :||.||::|  ..||:|||||
51    ALGAGGLPMGRIVEIYGPESSGKTTLTLQVIAAAQREGKTCAFIDAEHAL 100

99    DPLYAKKLGVDVQELLVSQPDTGEQALEIVELLARSGAVDVIVVDSVAAL 148
      ||:||:|||||:::||.|||||||||||||  |||||||||||||||||
101   DPIYARKLGVDIDNLLCSQPDTGEQALEICDALARSGAVDVIVVDSVAAL 150

149   VPKAEIEGEMGDQHVP.PARLMSQALRKLTAVLSKSNTAAIFINQVREKV 197
      .|||||||||:||  |:.  :||:||||:|||.:  |..|||   |||||:| |:
151   TPKAEIEGEIGDSHMGLAARMMSQAMRKLAGNLKQSNTLLIFINQIRMKI 200

198   GVMYGNPETTPGGRALKFYSSVRLDVRKSGQPIKVGNEAVGIKVKVKVVK 247
      |||:||||||.||.|||||.|||||:|:  |  ::|  |:::.||  ...:||||
201   GVMFGNPETTTGGNALKFYASVRLDIRRIG.AVKEGENVVGSETRVKVVK 249

248   NKLAPPFREAELEIYFGRGLDPVMDLVNVAVAAGVIEKAGSWFSYGEHRL 297
      ||:|:||::||::|..:|  |::    :||::|  . :|||||.|:||  :.::
250   NKIAAPFKQAEFQILYGEGINFYGELVDLGVKEKLIEKAGAWYSYKGEKI 299

298   GQGKEKAAEYLRERPELLEEIRAKVLERADKVVLAAGRKRGSR*       340
      ||||..|..:|..:|:::.||  .||   ||
300   GQGKANATAWLKDNPETAKEIEKKVRELLLSNPNSTPDFSVDDSEGVAET 349

350   NEDF*     353
```

CLONING OF THE RECA GENE FROM THERMUS AQUATICUS YT-1

RELATED APPLICATIONS

This application is a continuation-in-part of application Ser. No. 08/041,341 filed Apr. 01, 1993, now abandoned which is a continuation of application Ser. No. 07/611,268, filed Nov. 9, 1990, now abandoned; this application is also a continuation-in-part of application Ser. No. 08/089,910, filed Jul. 12, 1993, which is a continuation of application Ser. No. 07/733,744, filed Jul. 24, 1991, now abandoned, which is a continuation-in-part of application Ser. No. 07/611,268, now abandoned. The disclosures of all of these related applications are hereby incorporated herein in their entirety by this reference thereto.

FIELD OF THE INVENTION

This invention relates to the cloning, expression and purification of proteins, specifically the recA analog from the thermophilic eubacteria, *Thermus aquaticus* YT-1.

BACKGROUND OF THE INVENTION

The RecA protein is a critical component in recombinational DNA repair, homologous genetic recombination and the cellular SOS response which occurs in response to DNA damage. The first RecA protein was purified from *E. coli* in 1965 by Clark and Margulies (*Proc. Natl. Acad. Sci.* (1965) 53:451) and has since been cloned and purified from many different organisms (Roca et al. *Biochem. Molec. Bio.* (1990) 25(6):415–456). Its role in genetic recombination is via a multi-step pathway involving the formation of a single-stranded nucleoprotein filament, DNA pairing and subsequent strand exchange to form heteroduplex DNA. RecA is directly involved in post-replication DNA repair and the induction of the SOS response by cleavage of the lexA repressor. RecA mediates a set of DNA strand exchange reactions in vitro by self-assembly into filaments, binding to both single-stranded (ss) and double-stranded (ds) DNA and hydrolysis of ATP.

The *E. coli* RecA gene and protein have been extensively characterized and numerous mutants have been isolated. Twenty-three recA-like proteins have been isolated from prokaryotes, both in closely related enteric bacteria as well as more distantly related prokaryotes such as cyanobacteria. These proteins exhibit amino acid sequence similarities to *E. coli* recA which range from 56% to 100% (Roca and Cox, 1990). The tertiary structure of these proteins has been conserved throughout the bacterial kingdom as measured by cross-reactivity with polyclonal antibodies raised against the *E. coli* K-12 recA protein. In addition, the uvsX protein of bacteriophage T4 exhibits significant structural and functional similarity to the *E. coli* protein (Story et al., (1993) *Science*, 259: 1892–1896). However, the T4 protein does not cross-react antigenically with antibodies raised against the *E. coli* recA protein and only has 23% identical amino acid residues (Fujisawa et al., (1985) *Nucleic Acids Res.*, 13:7473–7481).

Recently, two eukaryotic recA analogues from *S. cerevisiae*, rad 51 and dmc1, have been isolated and characterized (Shinohara et al., (1992) *Cell*, 69:457–470; Bishop et al., (1992) *Cell*, 69:439–456). Although rad51 and dmc1 proteins share regions of strong amino acid similarity with *E. coli* RecA and will bind to ssDNA and dsDNA in the presence of ATP, they do not possess detectable ATPase or DNA strand exchange activities. In addition, based on amino acid sequence analysis of dmc1 and T4 UvsX, and crystallographic data from *E. coli* recA, the folded dmc1 and T4 UvsX proteins appear similar to the three dimensional structure of *E. coli* RecA.

SUMMARY OF THE INVENTION

One embodiment of the present invention is the use of the recA protein from *T. aquaticus* in stabilizing DNA-DNA, DNA-RNA or RNA-RNA interactions in reactions which occur at high temperatures by increasing the stringency, and thus the specificity, of the annealing reaction. More specifically, the use of this invention in increasing the specificity of DNA and RNA hybridization in the polymerase chain reaction (PCR), Northern and Southern blotting and the DNA chip sequencing method is envisioned. It is also envisioned that any reaction requiring the annealing of homologous primers, DNA or RNA would be enhanced in the presence of a thermostable recA protein. The primers, DNA and RNA can be labeled in a manner known to those having ordinary skill in the art, such as through radiolabelling or the use of colorimetrically labeled molecules.

In one aspect, the present invention comprises an isolated oligonucleotide encoding *Thermus aquaticus* recA protein. This oligonucleotide can be either DNA or RNA. In one embodiment, the oligonucleotide can have the nucleotide sequence of SEQ ID NO:1 or a sequence complementary to the nucleotide sequence of SEQ ID NO:1. Alternatively, the oligonucleotide can have the nucleotide sequence of SEQ ID NO:1 in which the thymine ("T") moieties are replaced with uracil ("U"). In another embodiment of this aspect of the invention, the oligonucleotide encoding *Thermus aquaticus* recA protein is operably linked to a heterologous promoter in a prokaryotic expression vector. The prokaryotic expression vector can, for example, be pTrc99a. The expression vector can also be placed in a cell line in continuous culture.

Another aspect of the present invention relating to oligonucleotides comprises an isolated oligonucleotide which contains at least 18 nucleotides. The sequence of such an oligonucleotide according to this aspect of the invention corresponds to 18 consecutive nucleotides of SEQ ID NO:1. Also included in this aspect of the invention is an oligonucleotide containing at least 18 nucleotides which has a sequence that is complementary to 18 consecutive nucleotides from the sequence of SEQ ID NO:1.

A further aspect of the present invention comprises purified *Thermus aquaticus* recA protein. Preferably, such purified *Thermus aquaticus* recA protein has the amino acid sequence of SEQ ID NO:2.

In yet another aspect, the present invention comprises a method for hybridizing a primer to a template with increased binding affinity at a temperature above 45° C. This method comprises incubating the primer and the template at a temperature above 45° C. in the presence of isolated *Thermus aquaticus* recA and then permitting the primer and the template to bind to each other. In this method, the primer can be colorimetrically labeled, radiolabeled, or labeled in any other way known to the art. The temperature used in this method is also preferably below 70° C.

Another aspect of the invention comprises a method of improving the accuracy of sequencing DNA by the DNA chip method through the use of *T. aquaticus* recA protein. This method comprises hybridizing a target DNA sequence to oligonucleotides on a solid matrix at temperatures in the range of about 45° to about 70° C. in the presence of *T. aquaticus* recA.

Yet another aspect of the present invention comprises a method of producing a complementary oligonucleotide that is complementary to an oligonucleotide template. In this method, an oligonucleotide primer is used that is shorter than both the complementary oligonucleotide and the oligonucleotide template to which the primer is complementary. This method comprises the steps of: (a) providing an oligonucleotide primer, an oligonucleotide template, *T. aquaticus* recA, nucleotide triphosphates and a polymerase in a buffer; (b) allowing the primer to bind to the template in the presence of the *T. aquaticus* recA; and (c) extending the primer with the nucleotide triphosphates. The inclusion of *T. aquaticus* recA protein increases the specificity of the primer for the oligonucleotide template.

The foregoing method can, in one embodiment, be practiced as part of a gene amplification technique, such as Polymerase Chain Reaction (PCR), self-sustained sequence replication (3SR), beta-Q replicase (βQR), first strand synthesis with DNA polymerase, ligation amplification reaction or ligase-based amplification system (LAR/LAS) and reverse transcription. In the PCR embodiment, the oligonucleotide template is a single strand of a double-stranded oligonucleotide molecule that comprises a complementary oligonucleotide template. This complementary oligonucleotide template is complementary to the oligonucleotide template. A second oligonucleotide primer is also added to the buffer used in this method. Specifically, the method in this embodiment of the invention comprises the additional steps of: (i) denaturing the double-stranded oligonucleotide molecule; (ii) allowing the second primer to bind to the complementary oligonucleotide template in the presence of the *T. aquaticus* recA; (iii) extending the second primer with the nucleotide triphosphates: and (iv) repeating steps (i), (b), (ii), (c) and (iii). The inclusion of *T. aquaticus* recA increases the specificity of the second primer for the complementary oligonucleotide template. This method can alternatively be practiced by raising the temperature of the buffer in the denaturing step, and by performing steps (i), (b), (ii), (c) and (iii) at a temperature lower than that used for the denaturing step. In another embodiment, the nucleotide triphosphates used in this method can comprise deoxynucleotide triphosphates, the oligonucleotide can comprise DNA, and the polymerase can comprise DNA polymerase.

DETAILED DESCRIPTION OF THE INVENTION

We have cloned the recA gene from the thermophilic eubacteria, *Thermus aquaticus* YT-1 (Taq), and overexpressed this thermostable protein in *E. coli*. Analysis of the deduced amino acid sequence indicates that the Taq recA protein is 57% identical to the *E. coli* protein. The protein has been purified and preliminary characterization indicates an ATP-dependent single-stranded DNA binding activity. The recombinant protein also pairs homologous DNA strands to form stable joint molecules. Unlike previously cloned recA proteins, a thermostable analogue will be suitable for various procedures which require the enzyme to act at higher temperatures. For example, Taq recA can enhance the specificity (stringency) of base-pairing reactions between homologous DNA molecules, and therefore will be useful in hybridization-type reactions.

Specifically, this invention discloses the cloning, sequencing, and recombinant production of the *E. coli* recA analogue from the thermophilic bacterium *T. aquaticus*. This protein is functionally similar to the *E. coli* recA protein but we have discovered that it is able to function at much higher temperatures.

The *T. aquaticus* recA gene, vectors containing this sequence or fragments thereof, and protein purified from transformed cells will be useful in promoting increased specificity of hybridization between polynucleotides at higher temperatures.

For example, *T. aquaticus* recA can be used to increase the specificity of annealing one gene sequence to another. Specifically, reactions such as gene amplification reactions can be run with shorter oligonucleotides and at higher temperatures in the presence of *T. aquaticus* recA. Perhaps the best known or these gene amplification reactions is polymerase chain reaction (PCR); however, several other gene amplification reactions are known. These include self-sustained sequence replication (3SR), beta-Q replicase (βQR), and first strand synthesis with DNA polymerase, reverse transcription.

In PCR, in general, multiple copies of nucleic acid sequences corresponding to a starting nucleic acid sequence are produced through stepwise reactions of (i) reacting a single stranded template nucleic acid sequence with one or more primer sequences, deoxyribonucleoside triphosphates, an inducing agent (i.e., a DNA polymerase), to form a dual stranded nucleic acid sequence consisting of the template and complementary strands; (ii) separating the complementary strand from the template, through, for example, heat denaturization or enzymatic cleavage, and (iii) repeating the process to obtain the desired number of copies. See e.g., U.S. Pat. No. 4,683,202. PCR reactants would normally include the oligonucleotide primers and a DNA polymerase, preferably Taq polymerase, in an appropriate buffer.

Heat denaturation is the preferred method of denaturing DNA strands to obtain the highest amplification yields in the PCR process. Accordingly, reaction vessels must be extremely durable to accommodate both the relatively high temperatures of the denaturing step, and the combined effects of rising and falling temperatures between the steps.

In 3SR, the reaction depends on continuous cycling of the reverse transcription and RNA transcription reactions to replicate an RNA target molecule by means of cDNA intermediates. Pairs of oligonucleotides are used to prime cDNA synthesis. The tails on oligonucleotides indicate that these primers contain the promoter sequence for the T7 RNA polymerase. Synthesis of a double stranded cDNA which serves as a transcription template for T7 RNA polymerase is carried out. Complete cDNA synthesis is dependent on the digestion of the RNA in the intermediate RNA-DNA heteroduplex by RNase H. Transcription competent cDNAs yield antisense or sense RNA copies of the original target. These transcripts are then converted to cDNAs with reverse transcriptase containing double-stranded promoter sequences which can serve as templates for further RNA synthesis. 3SR reactants would therefore normally include oligonucleotides having a T7 RNA polymerase site, RNase H and reverse transcriptase in an appropriate buffer.

Another method of gene amplification is termed ligation amplification reaction or ligase-based amplification system (LAR/LAS). In this method, a double stranded DNA target is thermally denatured in the presence of two sets of complementary oligonucleotides. Each set of oligonucleotides is specific for one DNA strand and is designed to anneal to the target sequence at adjacent sites. After hybridization, the two oligonucleotides are joined by DNA ligase to form the product. The product is then separted from the target sequence by heat denaturation and both the ligation product and the target then serve as substrate for the next cycle of hybridization and ligation. The reactants in this type of amplification would include the four primers and DNA ligase in an appropriate buffer.

In the Beta-Q-Replicase method, RNA is amplified in a manner similar to the transcription-based amplification system (TAS). During βQR the target RNA molecule (or denatured DNA) is hybridized to one primer oligonucleotide that having a 5' recognition site for Qβ replicase between a T7 (or T3 or SPG) RNA polymerase binding site and a target-complementary sequence (TCS). A second primer, having the 3' recognition site for Qβ replicase in addition to the TCS, is then added, followed by reverse transcription to produce cDNA molecules with both the 3' and 5' Qβ replicase sites. T7 RNA polymerase is then added to transcribe the eDNA into RNA copies of the target molecule. Qβ replicase can then be added to use these RNA transcripts as templates for the synthesis of both sense and antisense RNA replication products. The βQR method uses reactants comprising Beta-Q replicase, a primer with the 5' βQR site, a primer with the 3' βQR site, reverse transcriptase, T7 RNA polymerase and the appropriate buffers.

For a review of the aforementioned and other gene amplification methods, see Kwoh et al., *American Biotechnology Laboratory*, 8:14–25 (1990), the disclosure of which is hereby incorporated by reference.

In all of the known gene amplification methods, specificity and efficacy can be improved through the introduction of *T. aquaticus* recA. Due to the increased strength of annealing exact base pairings mediated by *T. aquaticus* recA, shorter oligonucleotide sequences can be used to prime gene amplification reactions. In addition, the gene amplification reactions can be run at higher temperatures and stringencies since *T. aquaticus* recA will specifically hold together exact base pair matches, while reducing non-specific DNA base pairing.

This feature of the *T. aquaticus* recA protein provides an important utility which is lacking in other recA proteins cloned to date. Other recA proteins do not have the important thermostability of the *T. aquaticus* recA protein and therefore will not function at the temperatures required during procedures such as PCR. The ability of *T. aquaticus* recA to increase the stability of exact DNA base pairing at high temperatures is unexpected in that it was impossible to test other recA analogues due to their inactivity at temperatures greater than 37° C.

Many improvements of known procedures can be obtained by including *T. aquaticus* recA in the annealing reaction. For example, the method of DNA sequencing of a gene using a "DNA chip" can be improved by the inclusion of *T. aquaticus* recA. In this method a large number of octamers with overlapping sequences are prearranged onto a solid grid. A gene is then labeled and placed in an annealing reaction with the chip. Those sequences that anneal to the chip are then read by computer and analyzed to determine the nucleotide sequence of the entire gene. One of the major problems with this procedure is the non-specific binding associated with hybridizing an eight base-pair oligonucleotide to a long stretch of DNA such as a gene. By using the *T. aquaticus* recA protein of the present invention it will be possible to increase the stringency of the annealing reaction while still maintaining the specific base pairing of the octamers to the gene.

In other embodiments of the invention, fragments of the *T. aquaticus* recA clone consisting of at least 18 consecutive base pairs will be useful as gene amplification primers for isolating recA-like proteins from other organisms. These amplified genes can then have utility for determining whether proteins from other organisms can mediate DNA binding and strand exchange activities at higher temperatures.

A number of prokaryotic expression vectors for producing purified thermostable recA proteins are within the scope of the present invention. Virtually any expression vector known to those of ordinary skill in the art that is able to transform cells and express the *T. aquaticus* recA protein are within the scope of the present invention. By determining the gene sequence of *T. aquaticus* recA we can now introduce mutations in order to study structure-function relationships as they relate to binding ssDNA and stabilizing polynucleotide interactions at increased temperatures. Using well known techniques, we can determine whether various structural motifs or particular stretches of amino acids are important in conferring thermostability upon the *T. aquaticus* recA protein.

Since there are several highly conserved amino acid sequences among prokaryotic recA proteins, degenerate oligonucleotides homologous to regions of the *E. coli* recA protein that are either highly conserved or functionally significant were used as primers in a PCR reaction to amplify DNA products from *T. aquaticus* genomic DNA as described in the following example:

EXAMPLE 1

Isolation of the *T. aquaticus* recA Gene

*T. aquaticus* cell cultures (American Type Culture Collection #25105) were grown at 70° C. in Thermus medium (4 g/l yeast extract, 8 g/l polypeptone (BBL 11910), 2 g/l NaCl, pH 7.5). *T. aquaticus* genomic DNA was prepared as described previously (Lawyer et al., (1989) *J. Biol. Chem.*, 264:6427–6437). Degenerate and non-degenerate oligonucleotides for PCR and DNA sequencing were synthesized by the phosphoramidite method on an Applied Biosystems Model 380B DNA synthesizer. Double-stranded DNA fragments were isolated by PCR (Perkin-Elmer Cetus) and were random prime labeled with the Arabion Decaprime DNA labeling kit for probing Southern blots and plaque hybridization. Degenerate primers used to amplify recA-related fragments from *T. aquaticus* genomic DNA had the following sequences, where all symbols, including those other than A, T, G or C, are given their standard meanings stated in 37 C.F.R. § 1.822(b)(1):

5'-GGGGAATTCDCCRGTRGTKGTYTCSGO-3' (SEQ ID NO:3)

5'-GGGGAATTCGTBRTKGAYTCDST-3' (SEQ ID NO:4)

A 210 base pair fragment was isolated by the PCR using primers having SEQ ID NOS:3 and 4. The 210 bp fragment was then sequenced and shown to have 68% similarity at the DNA level and 73% similarity at the amino acid level compared to the respective region in *E. coli* recA. After nucleotide sequencing, the 210 bp fragment was random-prime labeled by well known methods and used as a probe on Southern blots having *T. aquaticus* genomic DNA digested with several different restriction enzymes. The probe hybridized to a 1.4 kilobase (kb) SacI fragment on Southern blots.

Subsequently, a SacI *T. aquaticus* genomic DNA library was constructed in λZAPII (Stratagene) and probed with the aforementioned 210 bp fragment. Primary plaque hybridization yielded 7 positive plaques. Four of the 7 plaques were plaque purified and clones were excised by in vivo excision to germrate the cloned fragments in the pBluescript vector. A 1,4 12 base pair fragment which carried the *T. aquaticus* recA gene was isolated by this method. This clone corresponded to the exact size expected based on the Southern hybridization results. DNA sequencing reactions were performed using Sequenase (United States Biochemical). Recombinant clones were sequenced on both strands to determine the orientation of inserts. Computer analysis of nucleotide and amino acid primary sequences was by the University of Wisconsin Genetics Computer Group (UWGCG) Sequence Analysis package (BESTFIT program).

The 1.4 kb SacI insert was sequenced and found to contain an open reading frame of 1,023 base pairs with 61 base pairs upstream of the putative ATG codon and 328 base pairs downstream of a putative TGA termination codon. The *T. aquaticus* recA nucleotide sequence is shown herein as SEQ ID NO:1. The open reading frame encoded a putative 340 amino acid protein with an estimated molecular weight of 36,361. The recA deduced amino acid sequence is shown as SEQ ID NO:2.

AMINO ACID COMPOSITION AND CODON USAGE

The amino acid composition of the *T. aquaticus* recA reflected the inherent differences in amino acid preferences between thermophilic and mesophilic proteins. Similar to other Thermus proteins analyzed to date, *T. aquaticus* recA has no cysteine residues. The elimination of thiol groups has previously been implicated in promoting thermal stability (Mozhaev and Martinek, (1984) *Enzymes Microb. Technol.*, 6:50–59). The number of proline residues, however, was significantly greater than that seen for *E. coli* recA (16 versus 10; Table 1). Since proline residues restrict rotational flexibility by interrupting α-helices, a more compact and rigid secondary and tertiary structure would be predicted. The number of polar amino acids, (i.e. serine, threonine) was lower than that found in *E. coli* recA (26% polar amino acids in *T. aquaticus* versus 31% in *E. coli*) while 50% of the amino acids in *T. aquaticus* recA were hydrophobic or nonpolar compared to 43% in *E. coli* recA. Substitution of hydrophilic amino acids by hydrophobic amino acids would tend to yield a more compact structure. These types of substitutions reduce the overall hydrophilicity and protein flexibility and have been implicated in stabilizing proteins at higher temperatures (Bowen et al., (1988) *Biochem. J.*, 284:509–517).

TABLE 1

| Codon Preferences for *T. aq.* and *E. Coli.* | | | |
|---|---|---|---|
| Amino acid | Codon | *T. aq.* | *E. coli* |
| Phe | TTT | 2 | 4 |
|  | TTC | 6 | 6 |
| Leu | TTA | 0 | 0 |
|  | TTG | 4 | 2 |
|  | CTT | 4 | 3 |
|  | CTC | 6 | 2 |
|  | CTA | 1 | 0 |
|  | CTG | 20 | 24 |
| Met | ATG | 7 | 10 |
|  | GTG | 0 | 0 |
| Val | GTT | 1 | 4 |
|  | GTC | 11 | 3 |
|  | GTA | 1 | 5 |
|  | GTG | 24 | 10 |
| Ser | TCT | 0 | 6 |
|  | TCC | 6 | 6 |
|  | TCA | 0 | 2 |
|  | TCG | 4 | 1 |
|  | AGT | 1 | 0 |
|  | AGC | 4 | 5 |
| Pro | CCT | 1 | 0 |
|  | CCC | 9 | 0 |
|  | CCA | 1 | 1 |
|  | CCG | 5 | 9 |
| Thr | ACT | 1 | 3 |
|  | ACC | 8 | 9 |
|  | ACA | 0 | 0 |
|  | ACG | 2 | 5 |
| Ala | GCT | 2 | 4 |
|  | GCC | 26 | 4 |
|  | GCA | 0 | 11 |
|  | GCG | 8 | 19 |
| Tyr | TAT | 0 | 0 |
|  | TAC | 6 | 7 |
| His | CAT | 0 | 0 |
|  | CAC | 3 | 2 |
| Gln | CAA | 0 | 1 |
|  | CAG | 11 | 12 |
| Asn | AAT | 0 | 1 |
|  | AAC | 8 | 14 |
| Lys | AAA | 1 | 21 |
|  | AAG | 27 | 6 |
| Asp | GAT | 1 | 9 |
|  | GAC | 12 | 11 |
| Glu | GAA | 3 | 21 |
|  | GAG | 28 | 9 |
| Cys | TGT | 0 | 2 |
|  | TGC | 0 | 1 |
| Trp | TGG | 1 | 2 |
| Arg | CGT | 0 | 12 |
|  | CGC | 5 | 2 |
|  | CGA | 0 | 0 |
|  | CGG | 10 | 0 |
|  | AGA | 1 | 0 |
|  | AGG | 5 | 0 |
| Gly | GGT | 0 | 17 |
|  | GGC | 19 | 16 |

TABLE 1-continued

Codon Preferences for T. aq. and E. Coli.

| Amino acid | Codon | T. aq. | E. coli |
|---|---|---|---|
| | GGA | 0 | 1 |
| | GGG | 17 | 1 |
| END | TGA | 1 | 0 |
| | TAA | 0 | 1 |

Figure 1:
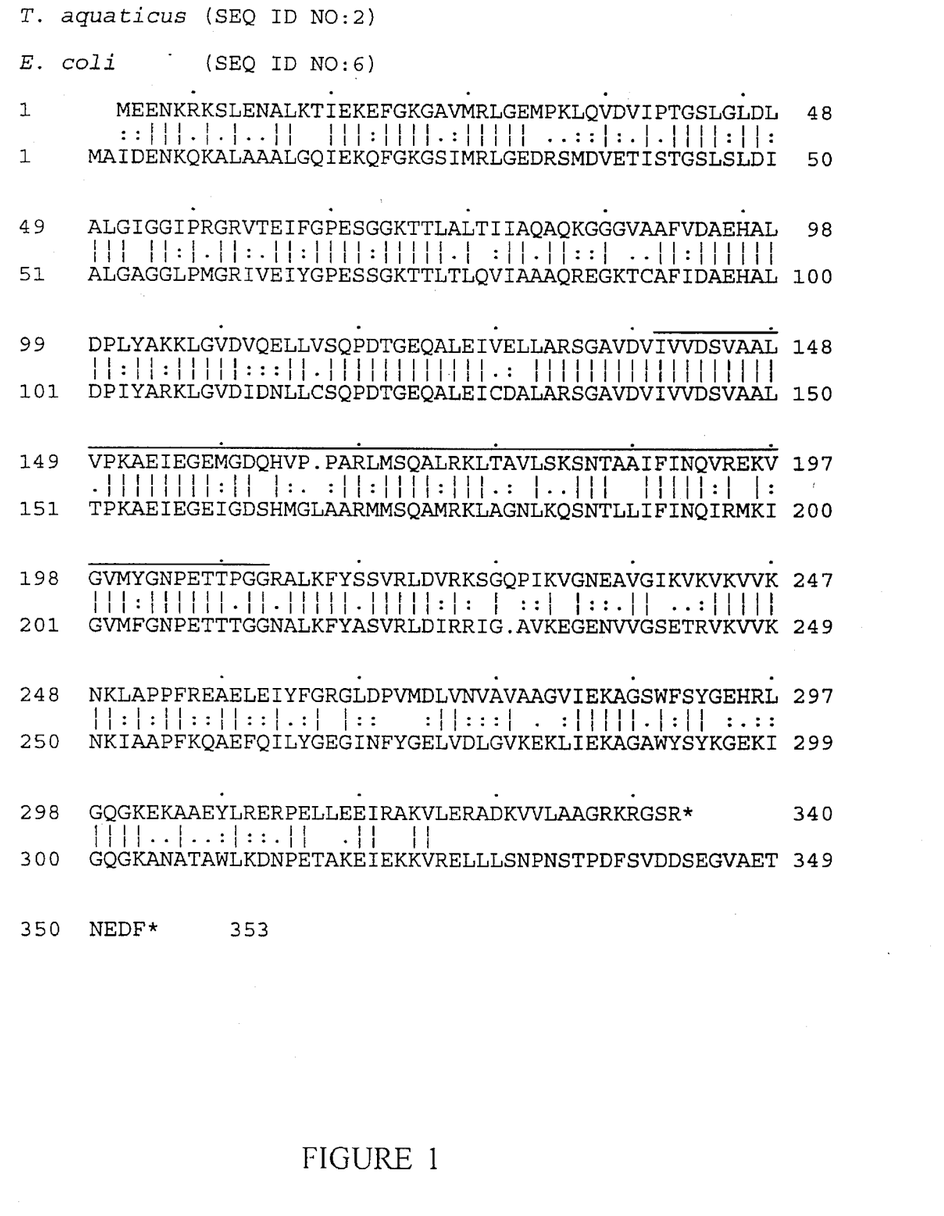
FIG. 1 compares the deduced amino acid sequence of *T. aquaticus* recA with *E. coli* recA. Vertical lines indicate identical amino acids between the two species. Conservative amino acid replacements are marked by two clots (:), indicating a comparison value ≧0.5 or single clots (.) for comparisons ≧0.1 (Default values described for BESTFIT sequence analysis with UWGCG). Gaps are introduced into the sequence to maximize the homolog. The 210 bp region isolated by PCR and used as a probe for Southern blots and plaque hybridization is indicated by a line over the sequence.

Sequence analysis at the nucleotide level of the open reading frame reflected a higher G/C content than in *E. coli*, similar to that reported for other Thermus genes (Lawyer et al., (1989) *J. Biol. Chem.*, 264:6427–6437; Kagawa et al., (1984) *J. Biol. Chem.*, 259:2956–2960; Nureki et al., (1991) *J. Biol. Chem.*, 266:3268–3277). The overall G/C content for *T. aquaticus* recA was 65% compared to 55% for *E. coli* recA. Additionally, the third letter in degenerate codons were highly G-C rich (Kagawa et al., (1984) *J. Biol. Chem.*, 259:2956–2960). This increased occurrence of G/C at the third position is reflected in the amino acid bias (i.e. the preference for amino acid codons that are G/C rich; (Table 1). Deduced nucleotide sequence alignments of *T. aquaticus* recA (SEQ ID NO:2) with *E. coli* recA (SEQ ID NO:6) showed (61% identity, while the amino acid identity was 57%, with 72% similarity. See FIG. 1. The overall percent identity at the amino acid level was lower due to the previously observed degeneracy at the third position of codons in thermophiles. The percent similarity reflected the overall conservation of the amino acid sequence of recA from *T. aquaticus*.

Following the cloning of a recA gene, a recombinant *T. aquaticus* recA-encoding prokaryotic expression vector was engineered as described below:

EXAMPLE 2

Construction of a Recombinant Expression Vector for T. aquaticus recA

The *T. aquaticus* recA gene, which is contained in the 1.4 kb fragment isolated by in vivo excision of a λZAPII library construct, was subcloned into the prokaryotic expression vector, pTRC99a (Pharmacia LKB). This expression plasmid carries a strong trc promoter [trp (−35) region and the lacUV5 (−10) region], a ribosome-binding site to facilitate translation initiation, an ampicillin resistance gene as a selectable marker, a lac repressor gene (lac I$^q$) to allow induction by isopropylthiogalactoside (IPTG) and strong transcription termination signals downstream of the multiple cloning region. Plasmid pTrc99a was digested with NcoI, treated with T4 DNA polymerase to eliminate the ATG initiation site on the vector and then dephosphorylated with calf intestinal phosphatase. The insert DNA was prepared by digesting the pBluescript plasmid with SacI to generate the 1.4 kb fragment, then treated with T4 DNA polymerase to generate blunt ends. The insert and plasmid DNA were blunt-end ligated with T4 DNA ligase at 14° C. by well known methods. The cloning sites were sequenced to ensure that translation would start from the correct ATG codon.

To express the recombinant *T. aquaticus* recA in *E. coli*, cells were transformed with the recombinant vector and the recA protein was purified as described in the following example:

EXAMPLE 3

Expression and Purification of T. aquaticus recA in E. coli

*E. coli* JM109 cells transformed with the recombinant plasmid were grown at 37° C. in LB medium (10 g/l tryptone, 10 g/l NaCl, 5 g/l yeast extract), containing 100 µg/ml ampicillin (Sigma) to mid-log phase ($OD_{600}$=0.4) and induced with 0.4 mM IPTG. The cells were harvested after 6 hours by centrifugation and then resuspended in lysis buffer (2 ml/g wet cells) containing 40 mM Tris-HCl, pH 8.0, 100 mM NaCl, 10 mM $MgCl_2$, 1 mM EDTA, 1 mM 2-mercaptoethanol.

Cells were disrupted by sonication and treated with DNase 1 (20 µg/ml) and 3 mM phenylmethysulfonyl fluoride (PMSF), a serine protease inhibitor, at 23° C. for 1 hour. A crude cell extract was obtained by centrifugation for 30 min at 10,000×g. Endogenous *E. coli* proteins were denatured by heat treatment at 70° C. for 45 minutes and removed from the cell extract by centrifugation at 16,000×g for 1 hour. The heat-purified extract was brought to 65% saturation with ammonium sulfate, precipitated and collected by centrifugation at 16,000×g for 1 hour. The pellet was then resuspended in phosphate buffer (20 mM potassium phosphate, pH 6.5, 10% (v/v) glycerol, 0.1 mM dithiothreitol, 0.1 mM EDTA).

The protein sample was dialyzed extensively to remove excess ammonium sulfate and applied to a 20 ml DEAE-Sephacel ion exchange column (Pharmacia LKB) equilibrated with phosphate buffer. A 0 to 0.4M linear gradient (300 ml total volume) of NaCl in phosphate buffer was applied to the column with the recA protein eluting at 180 mM NaCl. Fractions containing recA were pooled, dialyzed against phosphate buffer and applied to a 25 ml packed single-stranded DNA agarose affinity column (BRL) equilibrated with phosphate buffer. Non-specifically bound proteins were eluted with phosphate buffer containing 50 mM NaCl. Bound recA protein was eluted from the ssDNA agarose column with 1 mM ADP in phosphate buffer. The final pooled fraction was concentrated with Ficoll 400 (Pharmacia) and dialyzed against 20 mM Tris-HCl, pH 7.5, 50% (v/v) glycerol, 1.0 mM dithiothreitol, 0.1 mM EDTA, 100 mM KCl for storage at 4° C.

Coomassie blue-stained SDS polyacrylamide gels were used to monitor the purification scheme with the final protein sample representing an approximately 30-fold purification. The relative migration of the protein was in agreement with the expected molecular weight determination from the amino acid sequence. Immunodetection with antibodies against *E. coli* recA suggested that these antibodies recognized and cross-reacted with the major protein present, the *T. aquaticus* recA.

Assays were performed in order to determine whether the purified *T. aquaticus* recA protein exhibited properties similar to the *E. coli* recA protein, namely single-stranded DNA binding activity and DNA strand exchange activity as described in the following example:

EXAMPLE 4

Filter Binding Assay

The ability of the *T. aquaticus* recA protein to bind ssDNA was measured by the following method. Reactions were performed in the presence of the cofactors ADP and the nonhydrolyzable ATP analog, ATPλS, since under these conditions a stable, nondissociable protein:DNA complex is formed by *E. coli* recA (Hsieh et al., (1992) *Proc. Natl. Acad. Sci.* USA, 89:6492–6496).

Nitrocellulose membranes (Millipore; 0.45 µM pore size) were prepared by treatment with 0.3N NaOH for 30 minutes at room temperature then rinsed extensively with distilled water. Membranes were stored prior to use at room temperature in 50 mM Tris-HCl, pH 7.5, 12.5 mM MgCl$_2$. A 30-mer oligonucleotide ( 5'-CTGCAATGATACCGC-GAGACCCACGCTCAC-3'; SEQ ID NO:5) was 5'-end labeled with [λ-$^{32}$P]ATP and T4 polynucleotide kinase as described previously (Maniatis et al.). Reaction mixtures containing 20 mM Tris-HCl, pH 7.5, 0.4 mM dithiothreitol, 12.5 mM MgCl$_2$, 1.1 mM ADP, 0.3 mM ATPλS, 15 ng $^{32}$P-labeled oligonucleotide and 1.5 µg *T. aquaticus* recA were incubated for 30 minutes at various temperatures. Each reaction mixture was applied within 5 minutes to a filter under vacuum at room temperature and washed with 3 ml 20 mM Tris-HCl, pH 7.5, 12.5 mM MgCl$_2$. Filters were air dried and counted in a Hewlett Packard 2200CA scintillation counter.

Figure 2A:
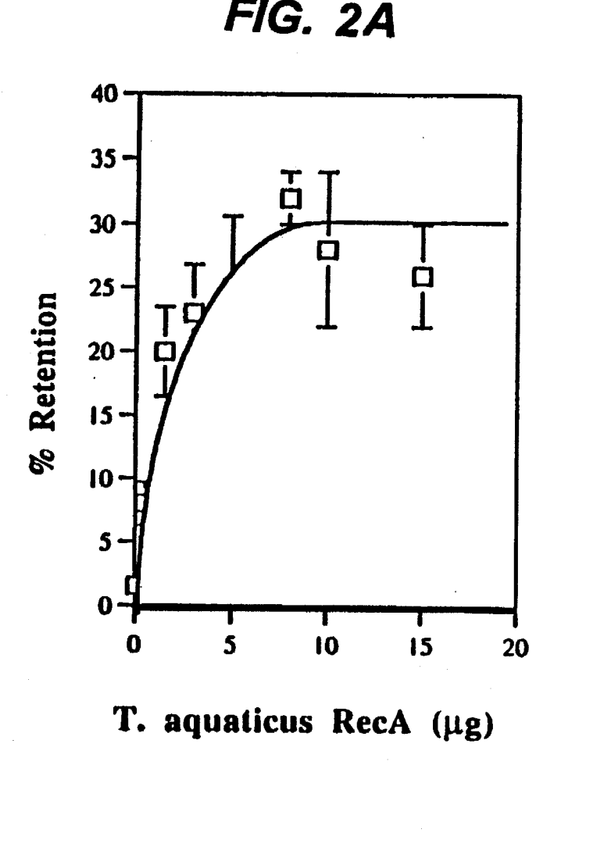
FIG. 2 illustrates the single stranded DNA filter binding assay. Panel A shows the percentage retention of Taq recA:ssDNA complex formation on nitrocellulose filters at 65° C. with increasing concentrations of Taq recA (0.1–15 µg). The amount of oligonucleotide used is 15 ng. Panel B shows the percentage retention of protein:ssDNA complex on nitrocellulose membranes at different temperatures for *E. coli* recA (-◇-) and *T. aquaticus* recA (-●-) (1.5 µg of each). Standard error values are indicated for each point. Background binding to filters was subtracted from each value obtained.
Figure 2B:
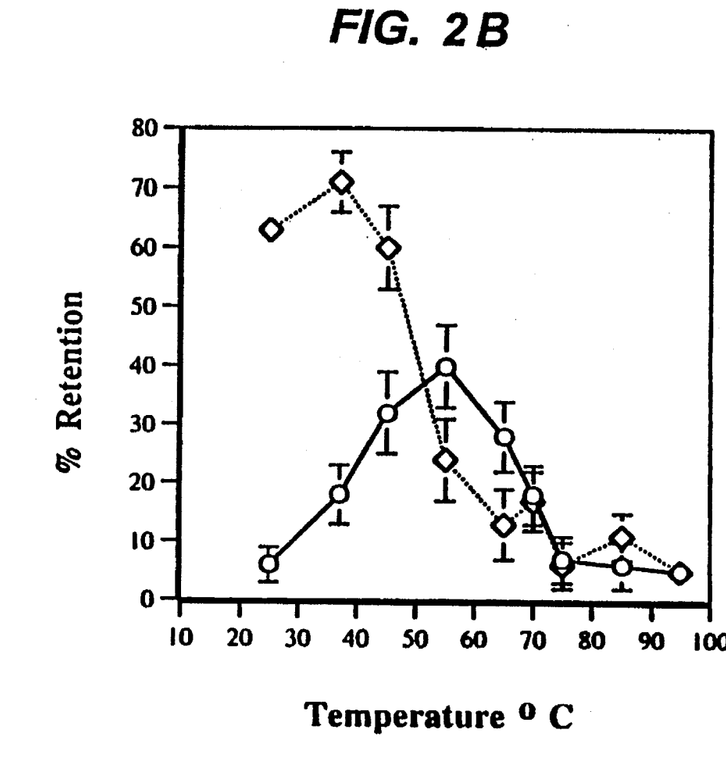

FIG. 2A shows the titration of *T. aquaticus* recA with 15 ng of an oligonucleotide DNA (30 mer) at 65° C. Maximum retention under these conditions occurred with 5 µg of *T. aquaticus* recA. To determine the optimal temperature of *T. aquaticus* recA binding to the $^{32}$P-labeled oligonucleotide, reactions were incubated at various temperatures from 25° C. to 95° C. and then vacuum filtered at room temperature (FIG. 2B). The filter binding assays indicated maximal amounts of complex formation at approximately 55° C. Unlike *E. coli* recA, *T. aquaticus* recA had an optimal ssDNA binding activity over a range of 45° C. to 70° C. Single-stranded DNA binding activity was reduced above 70° C., with less than 10% activity remaining above 75° C. (FIG. 2B). In contrast, ssDNA binding assays with *E. coli* recA showed approximately 75% retention at 37° C. and a marked reduction in binding activity above 45° C. and below 25° C. Similar to *E. coli* recA, ssDNA binding to protein was an ATP-dependent process. Filter binding reactions performed in the absence of ADP and ATPλS gave less than one percent binding activity.

In addition to the ssDNA binding assays, we also analyzed the ability of *T. aquaticus* recA to perform DNA strand exchange as explained below.

EXAMPLE 5

Strand Exchange Assay

The strand exchange assay conditions for this example was described previously (Hsieh and Camerini-Otero, (1989) *J. Biol. Chem.*, 264:5089–5097). M13mp18 viral DNA and BamHI-linearized M13mp18 replicative form DNA (50 ng each; New England Biolabs) were incubated with various amounts of *T. aquaticus* recA in 20 mM Tris-HCl, pH 7.5, 0.4 mM dithiothreitol, 12.5 mM MgCl$_2$, 1 mM ATP, and an ATP-regenerating system. RecA protein was incubated with ssDNA for 2 minutes at the appropriate temperature followed by a 2 minute incubation with 1 µg *E. coli* single-strand DNA binding (SSB) protein (Promega). Double stranded DNA was added and the reaction was further incubated at 65° C. for 15 minutes unless otherwise indicated. Reactions were deproteinized with 1% SDS and 10 mM EDTA in 10 mM Tris-acetate, pH 8.0, 10% glycerol, 0.04% bromophenol blue and analyzed on an 0.8% agarose gel containing 0.75 µg/ml ethidium bromide. Polaroid 665 negatives of ethidium bromide-stained gels were scanned on a Molecular Dynamics Scanning Laser Densitometer.

Figure 3:
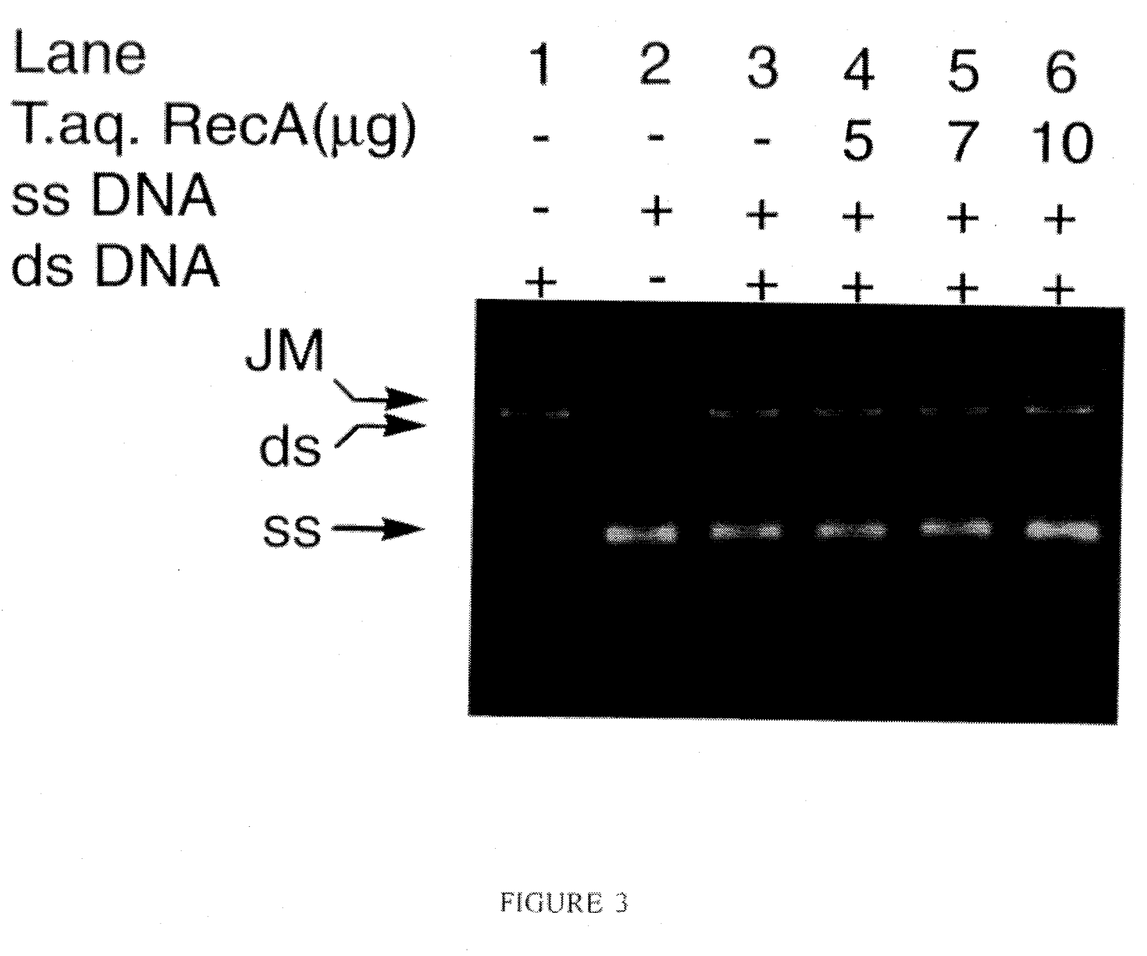
FIG. 3 illustrates the formation of joint molecules by *T. aquaticus* RecA containing 50 ng M13mp18 vital DNA and 50 ng of M13mp18 linear duplex DNA. Lane 1: M13mp18 linear duplex alone; Lane 2: M13mp18 vital DNA alone; Lane 3: control reaction in the absence of *T. aquaticus* recA; Lanes 4–6: addition of 5, 7, and 10 µg, respectively, of *T. aquaticus* recA protein. Abbreviations used include ss for single-stranded molecule, ds for double-stranded molecule, and JM for joint molecule.

The substrate DNAs in this reaction were linearized double-stranded M13mp18 and the homologous single-stranded circular M13mp18 DNA. The strand exchange reaction occurs by pairing a linear duplex DNA with homologous regions of the single-stranded circular DNA. Initiation of strand exchange, carried out by recA, requires the association of ssDNA with recA in an ATP-dependent fashion to form a nucleoprotein filament. This reaction also requires magnesium ions and ATP. SSB then binds to the exposed single-stranded region in order to increase its stability. Branch migration then forms a heteroduplex DNA product. Strand exchange products are visualized on ethidium bromide-stained agarose gels. The smaller substrate DNA migrates farther down the gel compared to the larger joint molecule (FIG. 3).

The results of the strand exchange assay with *T. aquaticus* recA indicate that the protein is able to mediate strand exchange between homologous ssDNA and dsDNA molecules to form a joint molecule as assessed by agarose gel electrophoresis.

We show preliminary evidence for strand exchange by *T. aquaticus* recA under reaction conditions that have been previously described for *E. coli* recA (Hsieh and Camerini-Otero, (1989) *J. Biol. Chem.*, 264:5089–5097). These data demonstrate that *T. aquaticus* recA can form joint molecules at 65° C. The formation of joint molecules by *T. aquaticus* recA at 65° C. is not as efficient as *E. coli* recA at 37° C. under similar reaction conditions, but represents a measurable strand exchange activity. *E. coli* recA has a 2–4 fold greater conversion to form joint molecules in the same amount of time as *T. aquaticus* recA. While not wishing to be bound by any particular explanation for this effect, we believe that one reason for the differences in conversion is the absence of a thermophilic analog to the *E. coli* single-stranded DNA binding protein (SSB) which acts to eliminate secondary structure barriers in ssDNA. Similar strand exchange experiments performed in the absence of ATP do not demonstrate any joint molecule formation.

An experiment to determine the optimal temperature for strand exchange by *E. coli* recA confirmed that optimal strand exchange occurred at 37° C., with an equivalent amount of activity at 25° C., near background levels at 45° C., and no activity at 55° C. and above, as measured by densitometric scanning of ethidium bromide-stained agarose gels. In a similar experiment with *T. aquaticus* recA, we observed a broader range of strand exchange activity from 37° C. to 65° C., with a peak activity at 65° C. These data are in relative agreement with the ssDNA filter binding studies described in the preceding section where peak ssDNA binding occurred near 55° C. under these conditions (FIG. 2B).

To determine whether the *T. aquaticus* recA protein was immunologically related to the *E. coli* recA protein, Western blots of *T. aquaticus* recA protein were immunostained with a polyclonal antibody against the *E. coli* recA protein as illustrated by the following example:

EXAMPLE 6

Immunochemical Detection of *T. aquaticus* recA

Protein samples were analyzed by electrophoresis on 12% Tris-glycine SDS polyacrylamide gels and transferred to nitrocellulose membranes. Nonspecific binding sites were blocked with 10% (w/v) nonfat dry milk, 0.1% (v/v) Tween 20 in phosphate buffered saline (PBS), pH 7.4. The filters were incubated with polyclonal anti-*E. coli* recA antibody purified with MAbTrap G (Pharmacia LKB; 1:6000) in 5% (w/v) nonfat dry milk, 0.1% (v/v) Tween 20 in PBS for one hour followed by incubation with anti-rabbit IgG conjugated alkaline phosphatase (AP) (Sigma; 1: 1200) in the same buffer for 1 hour. Color was developed with substrates provided by the Promega ProtoBlot Western Blot AP system.

The results indicated that the *T. aquaticus* and *E. coli* recA proteins were immunologically related since the immunostaining procedure using the polyclonal antibody generated against the *E. coli* protein detected the purified *T. aquaticus* recA protein. The *T. aquaticus* recA protein had a lower molecular weight than its *E. coli* counterpart and thus migrated faster on SDS polyacrylamide gels.

We envision the present invention being used to improve several technical methods as described in the following examples:

EXAMPLE 7

Reduction of PCR Artifacts Using *T. aquaticus* recA

A thermostable recA protein will be useful in stabilizing polynucleotide interactions in reactions which occur at high temperature by increasing the specificity (stringency) of the annealing reaction. In PCR, the normal annealing temperature range for primer and template is 42° C.–50° C. In the presence of *T. aquaticus* recA, this annealing temperature can be set to 65° C., thereby increasing the stringency of hybridization. Typically, 0.01 µg/µl to 5.0 µg/µl of *T. aquaticus* recA would be sufficient to obtain these desired effects. Under such conditions, fewer primer-template mismatches would occur and many PCR-generated artifacts could be avoided. In addition, the increased specificity would also reduce the concentration of primers necessary for successful product amplification and the length of primers necessary for annealing to specific sequences.

EXAMPLE 8

Use of *T. aquaticus* recA in Northern and Southern Blotting

A use for the thermostable recA protein could also be envisioned for increasing the specificity of DNA-DNA and DNA-RNA hybridization in Southern and Northern blotting, respectively. DNA or RNA is isolated from cells or tissues by conventional methods. DNA digested with various restriction enzymes and isolated RNA (either total RNA of mRNA) are analyzed by agarose gel electrophoresis and transferred to nitrocellulose or nylon membranes. Single-stranded oligonucleotides complementary to the desired DNA or RNA region are labeled, such as by end-labeling using $\lambda^{32}p$ ATP and T4 polynucleotide kinase, or other method known in the art. These labeled oligonucleotides are used to probe the blots at 65° C. in the presence of *T. aquaticus* recA, increasing the specificity of hybridization and decreasing the observed background signals, thus increasing the overall reliability of the results. Typically, 0.01 µg/µl to 5.0 µg/µl of *T. aquaticus* recA would be sufficient to obtain these desired effects.

EXAMPLE 9

The Use of recA in DNA Chip Technology

A newly-described method for sequencing DNA, called herein the "DNA chip" method, has the potential for sequencing DNA 100 times faster than is now possible (*Science* (1991) 253: 1489; and *Human Genome News*, January 1993, pp. 3). The method is based on the identification of target sequences by their complementary binding to oligonucleotide probes on an immobilized matrix. In this instance, the solid matrix is called a chip. If these immobilized oligonucleotides are, for example, octamers, then there would be 65,536 ($4^8$) possible oligonucleotides which would represent every possible sequence in a target DNA. Binding of the target DNA to the chip would result in a nested set of octamers and the overlaps could be used to order the sequences for computer analysis.

Since the proper hybridization between the target DNA and the oligonucleotides is critical to obtaining an accurate sequence, the reaction should be carried out at as high a stringency as possible which is where the *T. aquaticus* recA would be particularly useful in ensuring correct nucleotide pairing. Since the protein is active at 65° C., including it in the hybridization reaction would increase the fidelity of this state-of-the-art sequencing method. Typically, 0.01 µg/µl to 5.0 µg/µl of *T. aquaticus* recA would be sufficient to obtain these desired effects.

It is envisioned that any reaction making use of the annealing of homologous primers or DNA molecules to template DNA would be enhanced in the presence of a thermostable recA protein. Accordingly, the present invention includes the use of *T. aquaticus* RecA in connection with these other methods as well.

---

What is claimed is:

1. An isolated DNA molecule encoding *Thermus Aquaticus* recA protein as shown in SECt ID NO:2.

2. The isolated DNA molecule of claim 1, wherein said oligonucleotide has the nucleotide sequence of SEQ ID NO:1.

3. The DNA molecule of claim 1, wherein said DNA molecule is operably linked to a heterologous promoter in a prokaryotic expression vector.

4. The DNA molecule of claim 3, wherein said prokaryotic expression vector is pTrc99a.

5. The oligonucleotide of claim 3, wherein said vector is contained within cultured prokaryotic cells.

6. An isolated DNA molecule, wherein said DNA molecule has a sequence complementary to the nucleotide sequence of SEQ ID NO:1.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1412 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO ( i v ) ANTI-SENSE: NO ( v i i ) IMMEDIATE SOURCE:
    ( B ) CLONE: Taq recA ( i x ) FEATURE:
    ( A ) NAME/KEY: CDS
    ( B ) LOCATION: 62..1082

( x i ) SEQUENCE DESCRIPTION: SEQ ID NO:1:

```
GAGCTCAAGC CTAGGGGGCC CGTCTACACC ATTCTGGAAA AGTTCCCTTT GCGAGGTGAG            60

C ATG GAA GAG AAC AAG AGG AAG TCG CTG GAA AAC GCC CTC AAG ACC              106
  Met Glu Glu Asn Lys Arg Lys Ser Leu Glu Asn Ala Leu Lys Thr
  1               5                   10                  15

ATT GAA AAG GAG TTT GGC AAG GGG GCC GTC ATG CGC CTG GGG GAG ATG            154
Ile Glu Lys Glu Phe Gly Lys Gly Ala Val Met Arg Leu Gly Glu Met
                20                  25                  30

CCC AAG CTC CAG GTG GAC GTG ATC CCC ACG GGC TCC TTG GGC CTG GAC            202
Pro Lys Leu Gln Val Asp Val Ile Pro Thr Gly Ser Leu Gly Leu Asp
            35                  40                  45

CTG GCC CTG GGG ATC GGG GGC ATC CCC CGG GGG CGG GTC ACC GAG ATC            250
Leu Ala Leu Gly Ile Gly Gly Ile Pro Arg Gly Arg Val Thr Glu Ile
            50                  55                  60

TTT GGG CCG GAG TCG GGG GGC AAG ACC ACT TTG GCC CTG ACC ATC ATC            298
Phe Gly Pro Glu Ser Gly Gly Lys Thr Thr Leu Ala Leu Thr Ile Ile
        65                  70                  75

GCC CAG GCC CAG AAG GGG GGC GGG GTG GCG GCC TTC GTG GAC GCC GAG            346
Ala Gln Ala Gln Lys Gly Gly Gly Val Ala Ala Phe Val Asp Ala Glu
80              85                  90                  95

CAC GCC CTA GAC CCC CTT TAC GCC AAG AAG CTC GGG GTG GAC GTG CAG            394
His Ala Leu Asp Pro Leu Tyr Ala Lys Lys Leu Gly Val Asp Val Gln
                100                 105                 110

GAG CTT CTG GTC TCC CAG CCG GAC ACC GGG GAG CAG GCT TTG GAG ATC            442
Glu Leu Leu Val Ser Gln Pro Asp Thr Gly Glu Gln Ala Leu Glu Ile
            115                 120                 125

GTG GAG CTT CTG GCC CGC TCG GGG GCG GTG GAC GTG ATC GTG GTG GAT            490
Val Glu Leu Leu Ala Arg Ser Gly Ala Val Asp Val Ile Val Val Asp
            130                 135                 140

TCG GTG GCC GCT TTG GTG CCC AAG GCG GAG ATT GAG GGG GAG ATG GGG            538
Ser Val Ala Ala Leu Val Pro Lys Ala Glu Ile Glu Gly Glu Met Gly
        145                 150                 155

GAC CAG CAC GTG CCT CCA GCC CGG CTC ATG AGC CAG GCC CTG AGG AAG            586
Asp Gln His Val Pro Pro Ala Arg Leu Met Ser Gln Ala Leu Arg Lys
160                 165                 170                 175

CTG ACC GCC GTC CTC TCC AAG AGC AAC ACC GCC GCC ATC TTC ATC AAC            634
Leu Thr Ala Val Leu Ser Lys Ser Asn Thr Ala Ala Ile Phe Ile Asn
                180                 185                 190

CAG GTG CGG GAG AAG GTG GGG GTC ATG TAC GGC AAC CCC GAG ACC ACG            682
Gln Val Arg Glu Lys Val Gly Val Met Tyr Gly Asn Pro Glu Thr Thr
            195                 200                 205

CCG GGC GGC CGG GCC CTC AAG TTC TAC TCC AGC GTG CGC CTG GAC GTG            730
Pro Gly Gly Arg Ala Leu Lys Phe Tyr Ser Ser Val Arg Leu Asp Val
            210                 215                 220

CGC AAA AGC GGC CAG CCC ATC AAG GTG GGC AAC GAG GCC GTG GGC ATC            778
Arg Lys Ser Gly Gln Pro Ile Lys Val Gly Asn Glu Ala Val Gly Ile
        225                 230                 235

AAG GTC AAG GTC AAG GTG GTG AAG AAC AAG CTG GCC CCG CCC TTC CGG            826
Lys Val Lys Val Lys Val Val Lys Asn Lys Leu Ala Pro Pro Phe Arg
240                 245                 250                 255

GAG GCG GAG CTG GAG ATC TAC TTC GGC CGG GGC CTG GAC CCC GTT ATG            874
Glu Ala Glu Leu Glu Ile Tyr Phe Gly Arg Gly Leu Asp Pro Val Met
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| GAC | CTG | GTC | AAC | GTG | GCC | GTA | GCG | GCG | GGG | GTC | ATT | GAG | AAG | GCC | GGC | 922  |
| Asp | Leu | Val | Asn<br>275 | Val | Ala | Val | Ala | Ala<br>280 | Gly | Val | Ile | Glu | Lys<br>285 | Ala | Gly |      |
| TCC | TGG | TTC | TCC | TAC | GGC | GAG | CAC | CGC | CTG | GGC | CAG | GGC | AAG | GAG | AAG | 970  |
| Ser | Trp | Phe<br>290 | Ser | Tyr | Gly | Glu | His | Arg<br>295 | Leu | Gly | Gln | Gly<br>300 | Lys | Glu | Lys |      |
| GCG | GCC | GAG | TAC | CTG | AGG | GAG | CGG | CCG | GAG | CTT | CTG | GAG | GAG | ATC | CGG | 1018 |
| Ala | Ala | Glu<br>305 | Tyr | Leu | Arg | Glu | Arg<br>310 | Pro | Glu | Leu | Leu | Glu<br>315 | Glu | Ile | Arg |      |
| GCC | AAG | GTC | CTG | GAG | CGG | GCG | GAC | AAG | GTG | GTC | CTG | GCC | GCC | GGC | AGG | 1066 |
| Ala<br>320 | Lys | Val | Leu | Glu | Arg<br>325 | Ala | Asp | Lys | Val | Val<br>330 | Leu | Ala | Ala | Gly | Arg<br>335 |      |
| AAG | AGG | GGG | AGT | AGA | T   | GACCCTTCTG | GACCTGGTGC | TTTTGCTCCT | GGTCCTGGCC | | | | | | | 1122 |
| Lys | Arg | Gly | Ser | Arg<br>340 |     |     |     |     |     |     |     |     |     |     |     |      |

CTTCTCGCCG CCCTCTTCCT GAGGCGCAAG GGGGGTGAGG GTGAGGCGAG GGGGGAGGCC 1182

AGGGAGATCC TCGAGGCCGC CAAGCAGGCC AAGGAGGCCT GGAGTCTGCC CGCAAGGAGG 1242

CCAGGGAGAT CCTGGAGGCG GCCCGCAGGA GGCCAAGGGC CTGAGGGAGG AGGCCGAAAG 1302

CGCCTAAAGG CCTTCGGCAG GAGCTGGAGG AGGAGGCCCG GGCCCGGGCC TGGAGAAGGA 1362

ATCCAGGAGG CGCCTGGCCG AGGCGAGGAG CGCCTGAAGG GTAAAGGGAG 1412

(2) INFORMATION FOR SEQ ID NO:2:

(i) SEQUENCE CHARACTERISTICS:
        (A) LENGTH: 340 amino acids
        (B) TYPE: amino acid
        (D) TOPOLOGY: linear     (ii) MOLECULE TYPE: protein     (xi) SEQUENCE DESCRIPTION: SEQ ID NO:2:

| | | | | | | | | | | | | | | |
|---|---|---|---|---|---|---|---|---|---|---|---|---|---|---|
| Met<br>1 | Glu | Glu | Asn | Lys<br>5 | Arg | Lys | Ser | Leu | Glu<br>10 | Asn | Ala | Leu | Lys | Thr<br>15 | Ile |
| Glu | Lys | Glu | Phe<br>20 | Gly | Lys | Gly | Ala | Val<br>25 | Met | Arg | Leu | Gly | Glu<br>30 | Met | Pro |
| Lys | Leu | Gln<br>35 | Val | Asp | Val | Ile | Pro<br>40 | Thr | Gly | Ser | Leu | Gly<br>45 | Leu | Asp | Leu |
| Ala | Leu<br>50 | Gly | Ile | Gly | Gly | Ile<br>55 | Pro | Arg | Gly | Arg | Val<br>60 | Thr | Glu | Ile | Phe |
| Gly<br>65 | Pro | Glu | Ser | Gly | Gly<br>70 | Lys | Thr | Thr | Leu | Ala<br>75 | Leu | Thr | Ile | Ile | Ala<br>80 |
| Gln | Ala | Gln | Lys | Gly<br>85 | Gly | Gly | Val | Ala | Ala<br>90 | Phe | Val | Asp | Ala | Glu<br>95 | His |
| Ala | Leu | Asp | Pro<br>100 | Leu | Tyr | Ala | Lys | Lys<br>105 | Leu | Gly | Val | Asp | Val<br>110 | Gln | Glu |
| Leu | Leu | Val<br>115 | Ser | Gln | Pro | Asp | Thr<br>120 | Gly | Glu | Gln | Ala | Leu<br>125 | Glu | Ile | Val |
| Glu | Leu<br>130 | Leu | Ala | Arg | Ser | Gly<br>135 | Ala | Val | Asp | Val | Ile<br>140 | Val | Val | Asp | Ser |
| Val<br>145 | Ala | Ala | Leu | Val | Pro<br>150 | Lys | Ala | Glu | Ile | Glu<br>155 | Gly | Glu | Met | Gly | Asp<br>160 |
| Gln | His | Val | Pro | Pro<br>165 | Ala | Arg | Leu | Met | Ser<br>170 | Gln | Ala | Leu | Arg | Lys<br>175 | Leu |
| Thr | Ala | Val | Leu<br>180 | Ser | Lys | Ser | Asn | Thr<br>185 | Ala | Ala | Ile | Phe | Ile<br>190 | Asn | Gln |

| | | | | | | | | | | | | | |
|---|---|---|---|---|---|---|---|---|---|---|---|---|---|
| Val | Arg | Glu | Lys | Val | Gly | Val | Met | Tyr | Gly | Asn | Pro | Glu | Thr | Thr | Pro |
| | | 195 | | | | | 200 | | | | | 205 | | | |
| Gly | Gly | Arg | Ala | Leu | Lys | Phe | Tyr | Ser | Ser | Val | Arg | Leu | Asp | Val | Arg |
| | 210 | | | | | 215 | | | | | 220 | | | | |
| Lys | Ser | Gly | Gln | Pro | Ile | Lys | Val | Gly | Asn | Glu | Ala | Val | Gly | Ile | Lys |
| 225 | | | | | 230 | | | | | 235 | | | | | 240 |
| Val | Lys | Val | Lys | Val | Val | Lys | Asn | Lys | Leu | Ala | Pro | Pro | Phe | Arg | Glu |
| | | | | 245 | | | | | 250 | | | | | 255 | |
| Ala | Glu | Leu | Glu | Ile | Tyr | Phe | Gly | Arg | Gly | Leu | Asp | Pro | Val | Met | Asp |
| | | | 260 | | | | | 265 | | | | | 270 | | |
| Leu | Val | Asn | Val | Ala | Val | Ala | Ala | Gly | Val | Ile | Glu | Lys | Ala | Gly | Ser |
| | | 275 | | | | | 280 | | | | | 285 | | | |
| Trp | Phe | Ser | Tyr | Gly | Glu | His | Arg | Leu | Gly | Gln | Gly | Lys | Glu | Lys | Ala |
| | 290 | | | | | 295 | | | | | 300 | | | | |
| Ala | Glu | Tyr | Leu | Arg | Glu | Arg | Pro | Glu | Leu | Leu | Glu | Glu | Ile | Arg | Ala |
| 305 | | | | | 310 | | | | | 315 | | | | | 320 |
| Lys | Val | Leu | Glu | Arg | Ala | Asp | Lys | Val | Val | Leu | Ala | Ala | Gly | Arg | Lys |
| | | | | 325 | | | | | 330 | | | | | 335 | |
| Arg | Gly | Ser | Arg | | | | | | | | | | | | |
| | | | 340 | | | | | | | | | | | | |

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: cDNA    ( i i i ) HYPOTHETICAL: NO     ( i v ) ANTI-SENSE: NO     ( x i ) SEQUENCE DESCRIPTION: SEQ ID NO:3:

GGGGAATTCC CGTGTGTTCG G                21

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: cDNA    ( i i i ) HYPOTHETICAL: NO     ( i v ) ANTI-SENSE: NO     ( x i ) SEQUENCE DESCRIPTION: SEQ ID NO:4:

GGGGAATTCG TTGATCT                17

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear     ( i i ) MOLECULE TYPE: cDNA    ( i i i ) HYPOTHETICAL: NO ( i v ) ANTI-SENSE: NO ( x i ) SEQUENCE DESCRIPTION: SEQ ID NO:5:

CTGCAATGAT ACCGCGAGAC CCACGCTCAC 30

( 2 ) INFORMATION FOR SEQ ID NO:6:

( i ) SEQUENCE CHARACTERISTICS:
        ( A ) LENGTH: 353 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: N-terminal     ( x i ) SEQUENCE DESCRIPTION: SEQ ID NO:6:

```
Met Ala Ile Asp Glu Asn Lys Gln Lys Ala Leu Ala Ala Ala Leu Gly
 1               5                  10                  15

Gln Ile Glu Lys Gln Phe Gly Lys Gly Ser Ile Met Arg Leu Gly Glu
                20                  25                  30

Asp Arg Ser Met Asp Val Glu Thr Ile Ser Thr Gly Ser Leu Ser Leu
            35                  40                  45

Asp Ile Ala Leu Gly Ala Gly Gly Leu Pro Met Gly Arg Ile Val Glu
        50                  55                  60

Ile Tyr Gly Pro Glu Ser Ser Gly Lys Thr Thr Leu Thr Leu Gln Val
65                  70                  75                  80

Ile Ala Ala Ala Gln Arg Glu Gly Lys Thr Cys Ala Phe Ile Asp Ala
                85                  90                  95

Glu His Ala Leu Asp Pro Ile Tyr Ala Arg Lys Leu Gly Val Asp Ile
               100                 105                 110

Asp Asn Leu Leu Cys Ser Gln Pro Asp Thr Gly Glu Gln Ala Leu Glu
           115                 120                 125

Ile Cys Asp Ala Leu Ala Arg Ser Gly Ala Val Asp Val Ile Val Val
       130                 135                 140

Asp Ser Val Ala Ala Leu Thr Pro Lys Ala Glu Ile Glu Gly Glu Ile
145                 150                 155                 160

Gly Asp Ser His Met Gly Leu Ala Ala Arg Met Met Ser Gln Ala Met
               165                 170                 175

Arg Lys Leu Ala Gly Asn Leu Lys Gln Ser Asn Thr Leu Leu Ile Phe
           180                 185                 190

Ile Asn Gln Ile Arg Met Lys Ile Gly Val Met Phe Gly Asn Pro Glu
       195                 200                 205

Thr Thr Thr Gly Gly Asn Ala Leu Lys Phe Tyr Ala Ser Val Arg Leu
210                 215                 220

Asp Ile Arg Arg Ile Gly Ala Val Lys Glu Gly Glu Asn Val Val Gly
225                 230                 235                 240

Ser Glu Thr Arg Val Lys Val Val Lys Asn Lys Ile Ala Ala Pro Phe
               245                 250                 255

Lys Gln Ala Glu Phe Gln Ile Leu Tyr Gly Glu Gly Ile Asn Phe Tyr
           260                 265                 270

Gly Glu Leu Val Asp Leu Gly Val Lys Glu Lys Leu Ile Glu Lys Ala
       275                 280                 285
```

-continued

| | Gly | Ala 290 | Trp | Tyr | Ser | Tyr | Lys 295 | Gly | Glu | Lys | Ile | Gly 300 | Gln | Gly | Lys | Ala |
| Asn 305 | Ala | Thr | Ala | Trp | Leu 310 | Lys | Asp | Asn | Pro | Glu 315 | Thr | Ala | Lys | Glu | Ile 320 |
| Glu | Lys | Lys | Val | Arg 325 | Glu | Leu | Leu | Leu | Ser 330 | Asn | Pro | Asn | Ser | Thr 335 | Pro |
| Asp | Phe | Ser | Val 340 | Asp | Asp | Ser | Glu | Gly 345 | Val | Ala | Glu | Thr | Asn 350 | Glu | Asp |
| Phe | | | | | | | | | | | | | | | |